United States Patent
Barr et al.

(10) Patent No.: US 7,204,991 B2
(45) Date of Patent: Apr. 17, 2007

(54) PORPHYROMONAS GINGIVALIS RECOMBINANT PROTEINS AND TRUNCATIONS

(75) Inventors: Ian George Barr, Templestowe (AU); Larissa Czajkowski, Macleod (AU); Bruce Carter Ross, Coburg (AU)

(73) Assignee: CSL Limited, Parkville (AU)

( * ) Notice: Subject to any disclaimer, the term of this patent is extended or adjusted under 35 U.S.C. 154(b) by 104 days.

(21) Appl. No.: 10/283,024

(22) Filed: Oct. 28, 2002

(65) Prior Publication Data

US 2003/0215402 A1 Nov. 20, 2003

Related U.S. Application Data

(63) Continuation of application No. PCT/AU01/00482, filed on Apr. 27, 2001.

(30) Foreign Application Priority Data

Apr. 28, 2000 (AU) ................................. PQ7182

(51) Int. Cl.
- *A61K 39/02* (2006.01)
- *A61K 39/00* (2006.01)
- *A61K 38/00* (2006.01)
- *C07K 1/00* (2006.01)

(52) U.S. Cl. ................ 424/234.1; 424/184.1; 424/190.1; 514/2; 530/300; 530/350; 530/825; 530/806

(58) Field of Classification Search ................ 530/350, 530/300, 825, 806; 424/234.1, 184.1, 190, 424/190.1; 514/2
See application file for complete search history.

(56) References Cited

U.S. PATENT DOCUMENTS 5,475,097 A   12/1995   Travis et al. ................ 536/23.2
5,523,390 A   6/1996   Travis et al. ................ 536/23.2
2003/0083287 A1   5/2003   Burgess et al.

FOREIGN PATENT DOCUMENTS

WO   WO 97/16542   5/1997
WO   WO 99/29870   6/1999
WO   WO-01/47961 A1   7/2001

OTHER PUBLICATIONS

Ausubel, F.M. et al. eds. (1994). *Current Protocols in Molecular Biology*, John Wiley & Sons, Inc. pp. 1-12 (Table of Contents Only.).

Beck, J. et al. (Oct. 1996). "Periodontal Disease and Cardiovascular Disease," *J. Periodontol* 67(10):1123-1137.

Beck, J.D. et al. (Jul. 1998). "Periodontitis: A Risk Factor for Coronary Heart Disease?" *Annals of Periodontology* 3(1):127-141.

Di Donato, A. et al. (1993). "A Method For Synthesizing Genes and cDNAs by the Polymerase Chain Reaction," *Analytical Biochemistry* 212:291-293.

Sharp, P.M. et al. (1991). "Synonymous Codon Usage in *Saccharomyces cerevisiae*," *Yeast* 7:657-678.

Thorpe (1949). *Thorpe's Dictionary of Applied Chemistry*, Fourth Edition Longmans, Green and Co.: London, England. 9:510-511.

*Primary Examiner*—S. Devi
(74) *Attorney, Agent, or Firm*—Morrison & Foerster LLP

(57) ABSTRACT

The present invention relates to soluble *P. gingivalis* polypeptides derived from PG32 and PG33 and to polynucleotides encoding these polypeptides. The *P. gingivalis* polypeptides and nucleotides can be used in compositions for use in raising an immune response in a subject against *P. gingivalis* and treating or preventing or reducing the severity of the condition known as periodontitis or in other conditions related to infection with *P. gingivalis*.

10 Claims, 2 Drawing Sheets

PORPHYROMONAS GINGIVALIS RECOMBINANT PROTEINS AND TRUNCATIONS

CROSS REFERENCE TO RELATED APPLICATIONS

This application is a continuation of International Application No. PCT/AU01/00482, filed Apr. 27, 2001 and published in English on Nov. 8, 2001, which claims the benefit of Australian Application No. PQ 7182, filed Apr. 28, 2000, the contents of each are incorporated herein by reference.

FIELD OF THE INVENTION

The present invention relates to *P. gingivalis* nucleotide sequences and *P. gingivalis* polypeptides. The *P. gingivalis* polypeptides and nucleotides can be used in compositions for use in raising an immune response in a subject against *P. gingivalis* and treating or preventing or reducing the severity of the condition known as periodontitis or in other conditions related to infection with *P. gingivalis*.

BACKGROUND OF THE INVENTION

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is *P. gingivalis* as the recovery of this microorganism from adult periodontitis lesions can be up to 50% of the subgingival anaerobically cultivable flora, whereas *P. gingivalis* is rarely recovered, and then in low numbers, from healthy sites. A proportional increase in the level of *P. gingivalis* in subgingival plaque has been associated with an increased severity of periodontitis and eradication of the microorganism from the cultivable subgingival microbial population is accompanied by resolution of the disease. The progression of periodontitis lesions in non-human primates has been demonstrated with the subgingival implantation of *P. gingivalis*. These findings in both animals and humans suggest a major role for *P. gingivalis* in the development of adult periodontitis.

More recently there has been increasing linkage of periodontal disease and cardiovascular disease and therefore a link between *P. gingivalis* infection and cardiovascular disease. More information regarding this linkage can be found in Beck J D et al *Ann Periodontol.* 3:127–141, 1998 and Beck J, et al. *J. Periodontol.* 67: 1123–37, 1996.

*P. gingivalis* is a black-pigmented, anaerobic, asaccharolytic, proteolytic Gram-negative rod that obtains energy from the metabolism of specific amino acids. The microorganism has an absolute growth requirement for iron, preferentially in the form of haeme or its Fe(III) oxidation product haemin and when grown under conditions of excess haemin is highly virulent in experimental animals. A number of virulence factors have been implicated in the pathogenicity of *P. gingivalis* including the capsule, adhesins, cytotoxins and extracellular hydrolytic enzymes.

In order to develop an efficacious and safe vaccine to prevent, eliminate or reduce *P. gingivalis* colonisation it is necessary to identify and produce antigens that are involved in virulence that have utility as immunogens possibly through the generation of specific antibodies. Whilst it is possible to attempt to isolate antigens directly from cultures of *P. gingivalis* this is often difficult. For example as mentioned above, *P. gingivalis* is a strict anaerobe and can be difficult to isolate and grow. It is also known that, for a number of organisms, when cultured in vitro that many virulence genes are down regulated and the encoded proteins are no longer expressed. If conventional chemistry techniques were applied to purify vaccine candidates potentially important (protective) molecules may not be identified. With DNA sequencing, as the gene is present (but not transcribed) even when the organism is grown in vitro it can be identified, cloned and produced as a recombinant DNA protein. Similarly, a protective antigen or therapeutic target may be transiently expressed by the organism in vitro or produced in low levels making the identification of these molecules extremely difficult by conventional methods.

With serological identification of therapeutic targets one is limited to those responses which are detectable using standard methods such as Western Blotting or ELISA. The limitation here is both the level of response that is generated by the animal or human and determining whether this response is protective, damaging or irrelevant. No such limitation is present with a sequencing approach to the identification of potential therapeutic or prophylactic targets.

It is also well known that *P. gingivalis* produces a range of broadly active proteases (International Patent Application No PCT/AU96/00673, U.S. Pat. Nos. 5,475,097 and 5,523,390), which make the identification of intact proteins difficult because of their degradation by these proteases.

SUMMARY OF THE INVENTION

The present inventors have now identified fragments of the *P. gingivalis* PG32 and PG33 proteins which exhibit improved solubility when compared to the full length proteins. Using a murine lesion model of infection, the present inventors have found that these soluble fragments are capable of protecting against *P. gingivalis* challenge.

Accordingly, in a first aspect the present invention provides a soluble polypeptide, the polypeptide comprising a fragment of the sequence as shown in SEQ ID NO:3 or SEQ ID NO:4.

In a preferred embodiment of the first aspect, the fragment is derived from the region defined by residues 190 to 391 of SEQ ID NO:3 or the region defined by residues 210 to 380 of SEQ ID NO:4.

In a second aspect, the present invention provides a soluble polypeptide of the formula X-Y-Z, wherein Y is a soluble *P. gingivalis* fragment consisting of an amino acid sequence selected from the group consisting of residues 86 to 223 of SEQ ID NO:3, residues 191 to 322 of SEQ ID NO:3, residues 193 to 310 of SEQ ID NO:4, residues 191 to 306 of SEQ ID NO:3, residues 224 to 391 of SEQ ID NO:3, residues 213 to 380 of SEQ ID NO:4, residues 286 to 380 of SEQ ID NO:4, residues 224 to 306 of SEQ ID NO:3, residues 213 to 285 of SEQ ID NO:4, residues 281 to 384 of SEQ ID NO:3 and residues 306 to 372 of SEQ ID NO:4; and X and Z are optional and consist of amino acids or peptides which do not substantially adversely affect the solubility of the *P. gingivalis* fragment.

In a preferred embodiment of the second aspect, Y is a *P. gingivalis* fragment consisting of residues 224 to 391 of SEQ ID NO:3 or residues 213 to 380 of SEQ ID NO:4.

In a further preferred embodiment of the second aspect, X and/or Z are absent.

In a third aspect the present invention provides a soluble *P. gingivalis* polypeptide consisting essentially of a polypeptide having a sequence selected from the group consisting of residues 86 to 223 of SEQ ID NO:3, residues 191 to 322 of SEQ ID NO:3, residues 193 to 310 of SEQ ID NO:4, residues 191 to 306 of SEQ ID NO:3, residues 224 to 391 of SEQ ID NO:3, residues 213 to 380 of SEQ ID NO:4, residues 286 to 380 of SEQ ID NO:4, residues 224 to 306 of SEQ ID NO:3, residues 213 to 285 of SEQ ID NO:4, residues 281 to 384 of SEQ ID NO:3 and residues 306 to 372 of SEQ ID NO:4.

In a fourth aspect the present invention provides a chimeric or fusion construct comprising a soluble polypeptide of the first, second or third aspects.

In a fifth aspect the present invention provides an isolated DNA molecule, the DNA molecule comprising a nucleotide sequence which encodes a soluble fragment of the first, second or third aspects or which encodes a chimeric or fusion construct of the fourth aspect.

In a sixth aspect the present invention provides a recombinant expression vector comprising the DNA molecule of the fifth aspect of the present invention operably linked to a transcription regulatory element.

In a seventh aspect the present invention provides a cell comprising a recombinant expression vector of the sixth aspect.

In an eighth aspect the present invention provides a method for producing a *P. gingivalis* polypeptide comprising culturing a cell of the seventh aspect under conditions that permit expression of the polypeptide.

In a ninth aspect the present invention provides a composition for use in raising an immune response directed against *P. gingivalis* in a subject, the composition comprising an effective amount of at least one polypeptide of the first, second or third aspect, and/or at least one DNA molecule of the fifth aspect of the present invention, and a pharmaceutically acceptable carrier.

In a preferred embodiment of the ninth aspect, the pharmaceutically acceptable carrier is an adjuvant.

In a tenth aspect the present invention provides a method of reducing or preventing the incidence or severity of *P. gingivalis* infection in a subject comprising administering to the subject a composition according to the ninth aspect.

Given the increasing linkage of periodontal disease with cardiovascular disease (CVD) and the possible link therefore of *P. gingivalis* infection and CVD the composition of the eighth aspect of the present invention may also be used in a prophylactic therapy to reduce the incidence or severity of CVD or as an adjunct in treating CVD.

In an eleventh aspect the present invention provides an antibody raised against a soluble polypeptide of the first, second or third aspect.

The antibody of the eleventh aspect may be polyclonal or monoclonal.

In a twelfth aspect the present invention provides a composition comprising an antibody of the eleventh aspect and a pharmaceutically acceptable carrier.

In a preferred embodiment of the twelfth aspect, the composition is selected from the group consisting of a toothpaste, mouthwash, toothpowder, liquid dentifrice, mouthwash, troche, chewing gum, dental paste, gingival massage cream, gargle tablet, dairy product and other foodstuff composition.

In a thirteenth aspect the present invention provides a method for the treatment or prevention of *P. gingivalis* infection in a subject comprising passive vaccination of the subject with an antibody of the eleventh aspect of the present invention.

In a fourteenth aspect the present invention provides a diagnostic method for detecting the presence or absence of a *P. gingivalis* polypeptide in a sample, the method comprising contacting the sample with an antibody of the eleventh aspect under conditions sufficient for the antibody to form an immune complex with a *P. gingivalis* polypeptide in the sample, and detecting the presence or absence of an immune complex.

In a fifteenth aspect the present invention provides a diagnostic method for detecting the presence or absence of a *P. gingivalis* antibody in a sample, the method comprising contacting the sample with a soluble polypeptide of the first, second or third aspect under conditions sufficient for the soluble fragment of polypeptide to form an immune complex with an antibody in the sample, and detecting the presence or absence of an immune complex.

In a sixteenth aspect the present invention provides a kit comprising a soluble polypeptide of the first, second or third aspect and/or an antibody of the eleventh aspect.

DETAILED DESCRIPTION OF THE INVENTION

Figure 1A:
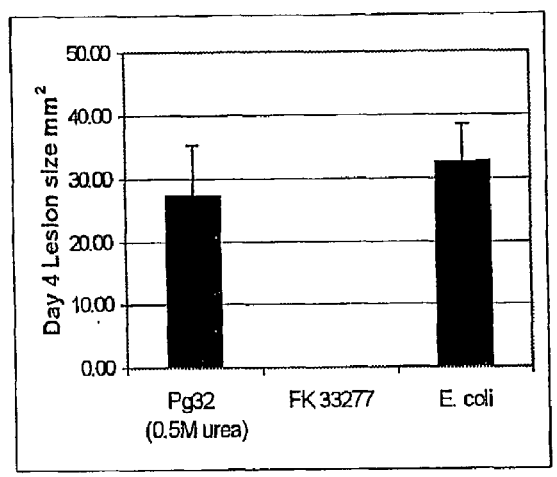
FIGS. 1A and 1B show the results from three separate experiments in which full length r-PG32 (Construct 1; aa21–391 in 0.5 M urea) (FIG.1*a*) and full length r-PG33 (Construct 2; aa22–380 in 2M urea) (FIG. 1*b*) were used to immunise mice and compared to fragments of r-PG32 (Construct 21; aa224–391 in PBS) and r-PG33 (Construct 22; aa213–380 in PBS) (FIG. 1*c*). Control mice were given formalin killed *P. gingivalis* strain 33277 whole cells (FK 33277) or whole *E. coli* lysate (*E. coli*).

The intra-oral bacterium *Porphyromonas gingivalis* contains on its surface the major outer membrane proteins PG32 and PG33. Truncated, soluble fragments of these proteins provide improved protection against *P. gingivalis* challenge in a mouse abscess model when compared to the full-length proteins.

Accordingly, in a first aspect the present invention provides a soluble fragment of the PG32 or PG33 polypeptide.

As used herein "soluble" means at least 5% soluble and preferably greater than 10% soluble as determined by the following method.

The levels and solubility of the recombinant proteins or their truncations can be assessed by taking a small amount of the recombinant *E. coli* cell culture (5–20 ml), pelleting the cells by centrifugation and resuspending the cells in 1.5 ml of TE buffer at pH 8.0. Cells are then sonicated with 2×10 sec bursts using a sonciator fitted with a microprobe (eg a Virosonic Digital 475 ultrasonic cell disruptor set at level 5, The VIRTIS Company, NY). Following centrifugation for 15 minutes (13,000 rpm) the supernatant is collected, this fraction represents the soluble fraction. The pellet is washed and then resuspended in TE buffer pH 8.0, this represents the insoluble fraction. Analysis of the various fractions to determine the level of recombinant protein present in each fraction can be carried out using SDS-PAGE and Western blot analysis and if the recombinant protein is purified, standard protein assays can also be used. The level of solubility is judged by determining the relative amounts of the recombinant protein in the "soluble" fraction compared to the amount in the "insoluble" fraction with the total representing 100% of the total recombinant protein recovered. In some cases non-ionic detergents such as NOG and CHAPS at levels of 0.1–1% w/v or 0.1–1% TWEEN-20 v/v can be added to the sonication process to aid in the solubilisation of the recombinant protein. For larger scale expression and purification purposes 500 ml E. coli cultures can be pelleted by centrifugation and resuspended in 40 ml of a suitable buffer (eg. 5 mM imidazole, 500 nM NaCl, 20 mM Tris-HCl, pH 7.9). Cells are then sonicated with 6×10 sec bursts using a microprobe (0.5") at a setting of 8 (Virosonic Digital 475 ultrasonic cell disrupter, The VIRTIS Company, NY). Following centrifugation for 15 minutes (13,000 rpm) the supernatant containing the soluble recombinant protein is collected for further analysis or for purification. If all the recombinant protein is found in the soluble fraction then this would represent 100% soluble protein and conversely if all of the recombinant protein is found in the insoluble fraction then this would represent 0% soluble protein.

The level of solubility of recombinant proteins or truncations expressed in yeast can be determined using the following procedure. A sample of the yeast culture expressing the recombinant protein can be harvested by centrifugation (30009 for 5 minutes) and resuspended in 500 ul breaking buffer (50 mM sodium dihydrogen orthophosphate, 1 mM EDTA, 5% glycerol, pH 7.4 containing 1 mM PMSF, 10 mM E-64, SIGMA). A 2.0 ml screw cap vial (BIOSPEC) is three quarters filled with 0.5 mm glass beads (BIOSPEC) and the remaining vial volume filled with resuspended cells. The mixture is then homogenised in a mini-beadbeater cell disrupter (eg BIOSPEC for 8×30 sec set at 5,000 rpm) with a 30 sec incubation on ice between runs. The beads are left to settle and the broken yeast cells recovered. Following centrifugation for 5 minutes (3,000 g) the supernatant is collected and this represents the soluble fraction. The remaining pellet resuspended in breaking buffer represents the insoluble fraction. In some cases non-ionic detergents such as NOG and CHAPS at levels of 0.1–1% w/v or 0.1–1% TWEEN-20 v/v can be added to aid in the solubilisation of the recombinant protein. Fractions are analysed using SDS-PAGE and Western blot analysis in a similar manner to the E. coli derived material in order to assess the relative amounts of recombinant protein present in the soluble and insoluble fractions.

In a preferred embodiment of the first aspect, the soluble fragment is derived from the region of the PG32 polypeptide which encompasses residues 190 to 391 of SEQ ID NO:3 or the region of the PG33 polypeptide which encompasses residues 210 to 380 of SEQ ID NO:4.

The present invention also provides a polypeptide of the formula X-Y-Z, wherein

Y is a soluble P. gingivalis fragment consisting of an amino acid sequence selected from the group consisting of residues 86 to 223 of SEQ ID NO:3, residues 191 to 322 of SEQ ID NO:3, residues 193 to 310 of SEQ ID NO:4, residues 191 to 306 of SEQ ID NO:3, residues 224 to 391 of SEQ ID NO:3, residues 213 to 380 of SEQ ID NO:4, residues 286 to 380 of SEQ ID NO:4, residues 224 to 306 of SEQ ID NO:3, residues 213 to 285 of SEQ ID NO:4, residues 281 to 384 of SEQ ID NO:3 and residues 306 to 372 of SEQ ID NO:4; and X and Z are optional and consist of amino acids or peptides which do not substantially adversely affect the solubility of the P. gingivalis fragment.

In a further preferred embodiment of the second aspect, X and Z are absent.

In yet another preferred embodiment the polypeptide of the second aspect is in the form of a chimeric or a fusion protein.

In a third aspect the present invention provides a soluble P. gingivalis polypeptide consisting essentially of a polypeptide having a sequence selected from the group consisting of residues 86 to 223 of SEQ ID NO:3, residues 191 to 322 of SEQ ID NO:3, residues 193 to 310 of SEQ ID NO:4, residues 191 to 306 of SEQ ID NO:3, residues 224 to 391 of SEQ ID NO:3, residues 213 to 380 of SEQ ID NO:4, residues 286 to 380 of SEQ ID NO:4, residues 224 to 306 of SEQ ID NO:3, residues 213 to 285 of SEQ ID NO:4, residues 281 to 384 of SEQ ID NO:3 and residues 306 to 372 of SEQ ID NO:4.

The present invention also encompasses soluble variants and derivatives of the polypeptides of the second or third aspects. The terms "variant" or "derivative" in relation to the amino acid sequences of the present invention includes any substitution of, variation of, modification of, replacement of, deletion of or addition of one (or more) amino acids from or to the sequence providing the resultant amino acid sequence is capable of raising an immune respond against P. gingivalis, preferably having at least 25 to 50% of the activity as the polypeptides presented in the sequence listings, more preferably at least substantially the same activity.

Amino acid sequence mutants of the polypeptides of the present invention can be prepared by introducing appropriate nucleotide changes into a nucleic acid sequence, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 30 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the antigenic determining region(s), and the active site(s). Other sites of interest are those in which particular residues obtained from various species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

TABLE 1

Exemplary Substitutions

| Original Residue | Exemplary Substitutions |
| --- | --- |
| Ala (A) | val; leu; ile; gly |
| Arg (R) | lys; gln; asn |
| Asn (N) | gln; his; lys; arg |
| Asp (D) | glu |
| Cys (C) | ser |
| Gln (Q) | asn; his |
| Glu (E) | asp |
| Gly (G) | pro; ala |
| His (H) | asn; gln; lys; arg |
| Ile (I) | leu; val; ala; met; phe |
| Leu (L) | ile; val; met; ala; phe |
| Lys (K) | arg; gln; asn |
| Met (M) | leu; phe; ile |
| Phe (F) | leu; val; ala; ile; tyr; trp |
| Pro (P) | gly |
| Ser (S) | thr |
| Thr (T) | ser |
| Trp (W) | tyr; phe |
| Tyr (Y) | trp; phe; thr; ser |
| Val (V) | ile; leu; met; phe; ala |

Furthermore, if desired, unnatural amino acids or chemical amino acid analogues can be introduced as a substitution or addition into the polypeptide of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, β-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Also included within the scope of the invention are biologically active fragments of the polypeptides of the present invention. By "biologically active fragment" we mean a soluble fragment of a sequence of the second or third aspects which retains at least one of the activities of the native polypeptide. Most preferably, a "biologically active fragment" of the present invention is capable of raising an immune response against P. gingivalis when the fragment is administered to a subject.

It will be appreciated that techniques for identifying a biologically active fragment or mutant of a polypeptide of the present invention which is capable of raising an immune response against P. gingivalis in a subject are well known in the art. For instance, substitutions and/or deletions can be made to the polypeptide of the present invention and the resulting fragment/mutant tested for its ability to raise an immune response against P. gingivalis in the subject.

The invention also provides chimeric or fusion proteins. As used herein, a "chimeric protein" or "fusion protein" comprises a first polypeptide of the present invention operatively linked to a partner polypeptide. The term "operatively linked" is intended to indicate that the first polypeptide and the partner polypeptide are fused in-frame to each other. The partner polypeptide can be fused to the N-terminus or C-terminus of the polypeptide of the present invention.

The partner polypeptide can be derived from the same or a different organism and may be the same of different to the first polypeptide. Accordingly, the fusion protein may comprise at least two polypeptides of the present invention.

In one embodiment, the fusion protein is a polypeptide of the present invention containing a heterologous signal sequence at its N-terminus. In certain host cells (e.g., mammalian host cells), expression and/or secretion of a polypeptide can be increased through use of a heterologous signal sequence.

In another embodiment, the fusion protein comprises a polypeptide of the present invention linked to a Maltose Binding Protein (MPB) or a glutathione transferase (GST) protein. MBP fusion proteins can be made using the New England Biolabs pMal expression system. Fusion of MBP or GST to recombinant proteins have been shown in some cases to facilitate the folding of the recombinant fusion partner and hence may increase solubility of the fusion protein compared to the non-fused recombinant P. gingivalis polypeptides of the present invention.

Preferably, a chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers.

Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A nucleic acid encoding a polypeptide of the present invention may be cloned into such an expression vector such that the fusion moiety is linked in-frame to a polypeptide of the present invention.

The present invention also provides nucleotide sequences coding for the soluble PG32 or PG33 fragments and functional equivalents of said nucleotide sequences and nucleic acid probes for said nucleotide sequences.

The invention also includes within its scope various applications and uses of the above nucleotides and recombinant products including chimeric or fusion recombinant polypeptides.

According to one embodiment of the present invention, using recombinant DNA techniques a gene sequence encoding a soluble PG32 or PG33 fragment is incorporated into an expression vector, and the recombinant vector is introduced into an appropriate host cell thereby directing the expression of the sequence in that particular host cell. The expression system, comprising the recombinant vector introduced into the host cell, can be used (a) to produce soluble PG32 or PG33 fragments which can be purified for use as immunogens in vaccine formulations; (b) to produce soluble PG32 or PG33 fragments to be used as antigens for diagnostic immunoassays or for generating P. gingivalis-specific antisera of therapeutic and/or diagnostic value; (c) or if the recombinant expression vector is a live virus such as vaccinia virus, the vector itself may be used as a live or inactivated vaccine preparation to be introduced into the host's cells for expression of soluble PG32 or PG33 fragments; (d) for introduction into live attenuated bacterial cells or genetically engineered commensal intra-oral bacteria which are used to express soluble PG32 or PG33 fragments to vaccinate individuals; (e) or for introduction directly into an individual to immunize against the encoded and expressed soluble PG32 or PG33 fragments. In particular the recombinant bacterial vaccine can be based on a commensal inhabitant of the human oral cavity or animal if the vaccine is to prevent periodontal disease in animals. The recombinant bacterial vaccine expressing soluble PG32 or PG33 fragments can be used to colonise the oral cavity, supragingival or subgingival plaque. The intra-oral bacterium can be isolated from the patient with periodontitis and genetically engineered to express the soluble PG32 or PG33 fragments. The soluble PG32 or PG33 fragments will stimulate the mucosal-associated lymphoid tissues (MALT) to produce specific antibodies to P. gingivalis.

Soluble PG32 or PG33 fragments can be used as immunogens in prophylactic and/or therapeutic vaccine formulations against pathogenic strains of P. gingivalis, whether the immunogen is chemically synthesized, purified from P. gingivalis, or purified from a recombinant expression vector system. Alternatively, a gene segment encoding a soluble PG32 or PG33 fragment may be incorporated into a bacterial or viral vaccine comprising recombinant bacteria or virus which is engineered to produce one or more soluble PG32 or PG33 fragments, or in combination with immunogenic epitopes of other pathogenic microorganisms. In addition, a gene encoding a soluble PG32 or PG33 fragment, operatively linked to one or more regulatory elements, can be introduced directly into humans to express the soluble fragment to elicit a protective immune response. A vaccine can also be based upon a recombinant component of a soluble PG32 or PG33 fragment incorporated into an appropriate vector and expressed in a suitable transformed host (eg. E. coli, Bacillus subtilis, Saccharomyces cerevisiae, COS cells, CHO cells and HeLa cells) containing the vector. The vaccine can be based on an intra-oral recombinant bacterial vaccine, where the recombinant bacterium expressing a soluble PG32 or PG33 fragment is a commensal inhabitant of the oral cavity.

A preferred embodiment of the invention is a vaccine based on a soluble fragment of the first aspect or a polypeptide of the second aspect and suitable adjuvant delivered by nasal spray, orally or by injection to produce a specific immune response against the PG32 or PG33 protein. A vaccine can also be based upon a recombinant component of soluble fragments of the first aspect or a polypeptide of the second aspect incorporated into an appropriate vector and expressed in a suitable transformed host (eg. E. coli, Bacillus subtilis, Saccharomyces cerevisiae, COS cells, CHO cells and HeLa cells) containing the vector.

The present invention also provides antibodies directed against the soluble polypeptides of the present invention.

When used herein, the term "antibody" includes fragments of whole antibodies which retain their binding activity for a target antigen. Such fragments include Fv, F(ab') and F(ab')2 fragments, as well as single chain antibodies (scFv). Furthermore, the antibodies and fragments thereof may be humanised antibodies, for example as described in EP-A-239400.

The soluble PG32 and PG33 polypeptides of the present invention can be used to generate antibodies using standard techniques. The animals used for antibody generation can be rabbits, goats, chickens, sheep, horses, cows etc. When a high antibody titre against a soluble fragment is detected by immunoassay the animals are bled or eggs or milk are collected and the serum prepared and/or antibody purified using standard techniques or monoclonal antibodies produced by fusing spleen cells with myeloma cells using standard techniques. The antibody (immunoglobulin fraction) may be separated from the culture or ascites fluid, serum, milk or egg by salting out, gel filtration, ion exchange and/or affinity chromatography, and the like, with salting out being preferred. In the salting out method the antiserum or the milk is saturated with ammonium sulphate to produce a precipitate, followed by dialyzing the precipitate against physiological saline to obtain the purified immunoglobulin fraction with the specific anti-PG32 or anti-PG33. The preferred antibody is obtained from the equine antiserum and the bovine antiserum and milk. In this invention the antibody contained in the antiserum and milk obtained by immunising the animal with the soluble fragments is blended into the oral composition. In this case the antiserum and milk as well as the antibody separated and purified from the antiserum and milk may be used. Each of these materials may be used alone or in combination of two or more. Antibodies against PG32 and PG33 can be used in oral compositions such as toothpaste and mouthwash. The antibodies can also be used for the early detection of P. gingivalis in subgingival plaque samples by a chairside Enzyme Linked Immunosorbent Assay (ELISA).

For oral compositions it is preferred that the amount of the above antibodies administered is 0.0001–50 g/kg/day and that the content of the above antibodies is 0.0002–10% by weight preferably 0.002–5% by weight of the composition. The oral composition of this invention which contains the above-mentioned serum or milk antibody may be prepared and used in various forms applicable to the mouth such as dentifrice including toothpastes, toothpowders and liquid dentifrices, mouthwashes, troches, periodontal pocket irrigating devices, chewing gums, dental pastes, gingival massage creams, gargle tablets, dairy products and other foodstuffs. The oral composition according to this invention may further include additional well-known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0, preferably 7.4. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle size of up to about 5 microns, a mean particle size of up to about 1.1 microns, and a surface area of up to about 50,000 $cm^2/gm.$, silica gel or colloidal silica, and complex amorphous alkali metal aluminosilicate.

When visually clear gels are employed, a polishing agent of colloidial silica, such as those sold under the trademark SYLOID as SYLOID 72 and SYLOID 74 or under the trademark SANTOCEL as SANTOCEL 100, alkali metal alumino-silicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by *Thorpe's Dictionary of Applied Chemistry*, (Volume 9, 4th Edition, pp. 510–511). The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10–30% by weight. Other polishing materials are typically present in amount of about 30–75% by weight.

In toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5–30% w/w of water, 0 to about 70% w/w of glycerine and about 20–80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as LAPONITE (e.g. CP, SP 2002, D) marketed by LAPORTE INDUSTRIES LIMITED. LAPONITE D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as NATROSOL), sodium carboxymethyl cellulose, and colloidal silica such as finely ground SYLOID (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, nonionic or ampholytic in nature which does not denature the antibody of the invention, and it is preferred to employ as the surface-active agent a detersive material which imparts to the composition detersive and foaming properties while not denaturing the antibody. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use with antibodies are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. PLURONIC materials).

Surface active agent is typically present in amount of about 0.1–5% by weight. It is noteworthy, that the surface active agent may assist in the dissolving of the antibody of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavor and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or such as glucose, sorbitol and the like.

The compositions of this invention also includes targeted delivery vehicles such as periodontal pocket irrigation devices, collagen, elastin, or synthetic sponges, membranes or fibres placed in the periodontal pocket or used as a barrier membrane or applied directly to the tooth root.

The present invention also provides a method of diagnosis for the presence of *P. gingivalis* characterised by the use of any one or a combination of an antibody or antigen as hereinbefore defined comprising the application of known techniques including for example, enzyme linked immunosorbent assay.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood preferred forms thereof will be described with reference to the following Examples.

EXAMPLE 1

Cloning and Analysis of the *P. gingivalis* Recombinant Proteins PG32 and PG33 and Fragments or Truncations of these Proteins (a) Cloning of the *P. gingivalis* Truncated Proteins PG32 (GENBANK accession number AF175714) and PG33 (GENBANK accession number AF175715) have previously been described as immunoreactive proteins of *P. gingivalis* strain W50. The complete DNA sequence and protein sequence for PG32 are given in SEQ ID NOs: 1 and 3 respectively and for PG33 in SEQ ID NOs: 2 and 4 respectively.

Both PG32 and PG33 recombinant proteins along with several truncations of these proteins (Table 2) were cloned and expressed in *E. coli*.

Using the oligonucleotide primers listed in Table 2, full length PG32, PG33 (with their leader sequences removed) and a number of fragments from PG32 and PG33 were PCR amplified from purified *P. gingivalis* W50 genomic DNA using Pfu DNA polymerase (PROMEGA) and a PTC-100 thermal cycler (MJ RESEARCH). The PCR reactions used the following conditions: 30 cycles of denaturation (95° C., 1 min), annealing (50° C., 2 min), and extension (72° C., 6 min). Each PCR product was proteinase K treated (BOEHRINGER MANNHEIM) and purified using the QIAquick PCR purification kit (QIAGEN). The DNA was then digested at the primer introduced restriction enzyme sites with EcoRI and NotI. The DNA fragment was purified following electrophoresis through a 1% low melting agarose gel (BIO-RAD) and extracted using the QIAEXII gel extraction kit (QIAGEN). The purified DNA was ligated into QIAEXII purified plasmid expression vector pET24a(+) (NOVAGEN) that had been previously digested with EcoRI and NotI. The ligation products were transformed into calcium competent *E. coli* BL21 DE3 cells (STRATAGENE) and transformants selected on LB containing 50 μg kanamycin. PG32, PG33 and truncations of these proteins were expressed from pET24a(+) containing a hexahistidine tag fused to the N-terminus of the expressed recombinant protein. Protein expression was induced by addition of IPTG and purified by nickel-affinity chromatography (see below).

TABLE 2

Oligonucleotide primers (F = forward and R = reverse)
used for the amplification of the nucleotide sequences encoding
PG32 and PG33 or portions of these genes. aa refers to the
amino acid number as given in SEQ ID NO:3 for PG32
and SEQ ID NO:4 for PG33.

| SEQ ID NO. | Recombinant Protein | F/R | Primers |
|---|---|---|---|
| 5  | PG32 (aa21-391) | F | 5' CGCAGAATTCCAGGAGAATACTGTACCGGCAACG 3' |
| 6  |                 | R | 5' CTATGCGGCCGCCTTGGAGCGAACGATTACAACAC 3' |
| 7  | PG33 (aa22-380) | F | 5' TGCAGAATTCCAAGAAGCTACTACACAGAACAAA 3' |
| 8  |                 | R | 5' CTATGCGGCCGCCTTCCGCTGCAGTCATTACTACAA 3' |
| 5  | PG32 (aa21-223) | F | 5' CGCAGAATTCCAGGAGAATACTGTACCGGCAACG 3' |
| 9  |                 | R | 5' TTTTGCGGCCGCCATCCCCTGGAATCCATT 3' |
| 10 | PG33 (aa22-212) | F | 5' TGCAGAATTCCAAGAAGCTACTACACAGAACAAA 3' |
| 11 |                 | R | 5' TTTTGCGGCCGCCATTACAGGGAAGTCTGC 3' |
| 12 | PG32 (aa86-223) | F | 5' TTTTGAATTCCCTTTCTTTGCAACTCGT 3' |
| 9  |                 | R | 5' TTTTGCGGCCGCCATCCCCTGGAATCCATT 3' |
| 13 | PG33 (aa84-212) | F | 5' TTTTGAATTCCCTTATTTCGGTACTCGT 3' |
| 11 |                 | R | 5' TTTTGCGGCCGCCATTACAGGGAAGTCTGC 3' |
| 5  | PG32 (aa21-152) | F | 5' CGCAGAATTCCAGGAGAATACTGTACCGGCAACG 3' |
| 14 |                 | R | 5' AAAAGCGGCCGCTTTGTGTTGGTAGCCAAC 3' |
| 10 | PG33 (aa22-150) | F | 5' TGCAGAATTCCAAGAAGCTACTACACAGAACAAA 3' |
| 15 |                 | R | 5' AAAAGCGGCCGCGAATTTATAACCAAATCC 3' |
| 16 | PG32 (aa153-306) | F | 5' TTTTGAATTCTTCATCGGTAGCGAATGG 3' |
| 17 |                  | R | 5' TTTTGCGGCCGCCAATTGATCTTTGTCCAC 3' |
| 18 | PG33 (aa151-285) | F | 5' TTTTGAATTCCATAGCGAAAACGCCAA 3' |
| 19 |                  | R | 5' TTTTGCGGCCGCGATACGGAAGTAAACCAC 3' |
| 20 | PG32 (aa191-322) | F | 5' TTTTGAATTCGCTCACTCCAATCTCAAT 3' |
| 21 |                  | R | 5' AAAAGCGGCCGCCTCGTTAGTTTCTTTTAC 3' |
| 22 | PG33 (aa193-310) | F | 5' TTTTGAATTCTTTGCCGGAAAGATGAAC 3' |
| 23 |                  | R | 5' AAAAGCGGCCGCTGCGTTGTTGGTCTTCGC 3' |
| 12 | PG32 (aa86-306) | F | 5' TTTTGAATTCCCTTTCTTTGCAACTCGT 3' |
| 17 |                 | R | 5' TTTTGCGGCCGCCAATTGATCTTTGTCCAC 3' |
| 13 | PG33 (aa84-285) | F | 5' TTTTGAATTCCCTTATTTCGGTACTCGT 3' |
| 19 |                 | R | 5' TTTTGCGGCCGCGATACGGAAGTAAACCAC 3' |
| 12 | PG32 (aa86-322) | F | 5' TTTTGAATTCCCTTTCTTTGCAACTCGT 3' |
| 21 |                 | R | 5' AAAAGCGGCCGCCTCGTTAGTTTCTTTTAC 3' |
| 13 | PG33 (aa84-310) | F | 5' TTTTGAATTCCCTTATTTCGGTACTCGT 3' |
| 23 |                 | R | 5' AAAAGCGGCCGCTGCGTTGTTGGTCTTCGC 3 |
| 16 | PG32 (aa153-322) | F | 5' TTTTGAATTCTTCATCGGTAGCGAATGG 3' |
| 21 |                  | R | 5' AAAAGCGGCCGCCTCGTTAGTTTCTTTTAC 3' |
| 18 | PG33 (aa151-310) | F | 5' TTTTGAATTCCATAGCGAAAACGCCAA 3' |
| 23 |                  | R | 5' AAAAGCGGCCGCTGCGTTGTTGGTCTTCGC 3' |
| 20 | PG32 (aa191-306) | F | 5' TTTTGAATTCGCTCACTCCAATCTCAAT 3' |
| 17 |                  | R | 5' TTTTGCGGCCGCCAATTGATCTTTGTCCAC 3' |
| 22 | PG33 (aa193-285) | F | 5' TTTTGAATTCTTTGCCGGAAAGATGAAC 3' |
| 19 |                  | R | 5' TTTTGCGGCCGCGATACGGAAGTAAACCAC 3' |
| 24 | PG32 (aa224-391) | F | 5' GATCGAATTCGCTACAGCAGGTCTTAATTTCC 3' |
| 6  |                  | R | 5' CTATGCGGCCGCCTTGGAGCGAACGATTACAACAC 3' |
| 25 | PG33 (aa213-380) | F | 5' GATCGAATTCGCTACAGCAGGTCTAACGTTCAA 3' |
| 8  |                  | R | 5' CTATGCGGCCGCCTTCCGCTGCAGTCATTACTACAA 3' |
| 26 | PG33 (aa286-380) | F | 5' GATCCGAATTCGAATAGTGCAAAGATTGAT 3' |
| 8  |                  | R | 5' CTATGCGGCCGCCTTCCGCTGCAGTCATTACTACAA 3' |

TABLE 2-continued

Oligonucleotide primers (F = forward and R = reverse)
used for the amplification of the nucleotide sequences encoding
PG32 and PG33 or portions of these genes. aa refers to the
amino acid number as given in SEQ ID NO:3 for PG32
and SEQ ID NO:4 for PG33.

| SEQ ID NO. | Recombinant Protein | F/R | Primers |
|---|---|---|---|
| 24 | PG32 (aa224-306) | F | 5' GATCGAATTCGCTACAGCAGGTCTTAATTTCC 3' |
| 17 | | R | 5' TTTTGCGGCCGCCAATTGATCTTTGTCCAC 3' |
| 25 | PG33 (aa213-285) | F | 5' GATCGAATTCGCTACAGCAGGTCTAACGTTCAA 3' |
| 19 | | R | 5' TTTTGCGGCCGCGATACGGAAGTAAACCAC 3' |
| 27 | PG32 (aa281-384) | F | 5' GATCGAATTCACTAAGACAGAAAATATACTGA 3' |
| 28 | | R | 5' TTTTGCGGCCGCACGATTCCAAGCTTTCTT 3' |
| 29 | PG33 (aa306-372) | F | 5' GATCGAATTCAAGACCAACAACGCACCGATCA 3' |
| 30 | | R | 5' TTTTGCGGCCGCACGATTCCAAGCGTTCTC 3' |

(b) Expression of Recombinant Proteins in *E. coli*

A single colony transformant was used to inoculate 20 mls of Luria-Bertani broth (LB) containing 50 μg/ml kanamycin and shaken at 37° C. overnight. This inoculum was then used to inoculate 500 ml of Terrific broth (containing potassium phosphates and 50 μg/ml kanamycin) and shaken at 37° C. until the optical density (OD600) was 2.0. The culture was induced with 0.1 mM IPTG. After a 1–4 hour induction period at 30° C. or 37° C. the culture was harvested by centrifuging at 4000 rpm for 10 min at 4° C. and the pellet was stored at −70° C. for determination of solubility of the recombinant protein.

(c) Determination of Solubility of Recombinant-proteins

The expression levels and solubility of r-PG32 or r-PG33 proteins or their truncations were assessed following IPTG induction. Approximately 14 ml of the recombinant *E. coli* cell culture was pelleted by centrifugation and resuspended in 1.5 ml of TE pH 8.0. Cells were then sonicated with 2×10 sec bursts using a microprobe at a setting of 5 (Virosonic Digital 475 ultrasonic cell disruptor, THE VIRTIS COMPANY, NY). Following centrifugation for 15 minutes (13, 000 rpm) the supernatant was collected, which represented the soluble fraction. The pellet was washed and then resuspended in TE pH 8.0, this represented the insoluble fraction. Analysis of the various fractions was carried out using Western blot analysis and SDS-PAGE. The results of these experiments are shown in Table 3. In some cases non-ionic detergents such as NOG and CHAPS at 0.1–1% were added to the sonication process to aid in the solubilisation of the recombinant protein. For large scale expression and purification purposes 500 ml *E. Coli* cultures were pelleted by centrifugation and resuspended in 40 ml of 1× binding buffer (5 mM imidazole, 500 nM NaCl, 20 mM Tris-HCl, pH 7.9). Cells were then sonicated with 6×10 sec bursts using a microprobe (0.5") at a setting of 8 (Virosonic Digital 475 ultrasonic cell disruptor, THE VIRTIS COMPANY, NY). Following centrifugation for 15 minutes (13,000 rpm) the supernatant containing the soluble recombinant protein was collected purified as outlined below.

(d) Isolation and Solubilisation of Inclusion Bodies or Insoluble Recombinant Proteins Where the r-protein was found to be insoluble as in the case of the full length PG32 (SEQ ID NO:3; residues 21–391) and PG33 (SEQ ID NO:4; residues 22–380), the recombinant *E. Coli* pellet was thawed on ice and resuspended in binding buffer, then sonicated and centrifuged at 20,000×g to collect the inclusion bodies. The pellet was resuspended in binding buffer and the process of sonication and centrifugation repeated twice more to release further protein. The pellet was then resuspended in binding buffer containing 6 M urea and incubated on ice for 2–3 hers stirring to completely dissolve proteins. Any remaining insoluble material was removed by centrifuging at 39,000×g for 20 min. The supernatant was filtered through a 0.45 μm membrane before column purification.

(e) Nickel-nitrilotriaectic Acid (In-NAT) Purification and Refolding of Recombinant Proteins Ni-NTA metal affinity chromatography was used to purify the recombinant proteins via the H6 tag. Briefly, proteins were batch bound to the equilibrated Ni-NTA resin (QIAGEN) which was poured into a small column and unbound proteins were eluted under gravity. The column was then washed with 10 ml of binding buffer followed by 6 ml of wash buffer (60 mM imidazole, 500 mM NaCl, 20 mM Tris-HCl, pH 7.9). The bound protein was then eluted in buffer containing 1M imidazole, 500 mM NaCl, 20 mM Tris-HCl, pH 7.9). If solubilised inclusion bodies or insoluble recombinant protein was being purified, 6 M urea was added to the above buffers.

(f) Renaturation of Recombinant Protein

For preparations not containing urea, the eluted protein fractions from the Ni-NTA resin were pooled before dialysis against 0.5 M Tris-HCl, 50 mM NaCl to remove traces of imidazole.

For preparations containing urea, the eluted protein fractions from the Ni-NTA resin were pooled and refolded by the step-wise dialysis from 6 M to 4 M to 2M to 0.5 M to 0 M urea contained in the following buffer 50 mM Tris-HCl, 0.5 M NaCl and 8% Glycerol. A minimum of 2 hr dialysis was carried out at each different urea concentration. Various detergents were also added to the dialysis buffer in some cases to improve solubility such as 0.5–1% NOG or 0.5%–1% CHAPS.

(g) Polyacrylamide Gel Electrophoresis and Western Blotting

SDS-PAGE was performed essentially as recommended by NOVEX. Samples were mixed with an equal volume of 2× sample reducing buffer (NOVEX), boiled for 10 min at 100° C. and applied to Tris-glycine 4–20% gels (NOVEX). Molecular weight standards (SeeBlueTM) were also purchased from NOVEX. Western blots were prepared by electroblotting proteins onto nitrocellulose for 1 hr at 100 volts following electrophoresis. Membranes were blocked with 5% skim milk-PBS before incubating with either anti-rabbit antibody diluted to {fraction (1/5000)} or with anti-rat antibody diluted to {fraction (1/1000)} in 5% skim milk-PBS. Membranes were later washed and incubated with a goat anti-rabbit-HRP conjugate (KPL) or a goat anti-mouse-HRP conjugate (KPL), washed and developed with TMB membrane peroxidase substrate (KPL).

EXAMPLE 2

Antisera

Polyclonal antiserum was raised to the purified recombinant proteins by dosing BALB/c mice with 2×20 µg of the PG32 (construct 21) recombinant protein in Freunds incomplete adjuvant (FIA; SIGMA) three weeks apart. Mice were bled one week after the second dose and the antiserum generated was used to screen Western blots of whole cell *P. gingivalis* W50 run under denaturing and reducing conditions. Antisera were also raised in rabbits by immunisation with 3 doses of either whole *P. gingivalis* cells (strain W50) or SARKOSYL insoluble enriched fractions (a method which enriches for outer membrane proteins of gram negative organisms) of *P. gingivalis* (strain W50) in FIA. Antisera were also raised in rats following immunisation with whole *P. gingivalis* W50 cells in Freunds Incomplete adjuvant. The rats were then challenged orally with live *P. gingivalis* cells (strain ATCC 33277) and bled 6 weeks later. These rats were later shown to be protected from alveolar bone loss around the molar teeth following challenge compared to the control rats.

TABLE 3

Determination of solubility, expression levels and Western Blot reactivity with PG32 and PG33 recombinant proteins and fragments.

| # | Construct in pET24a (+) | Expression Level* | Protein size (kDa) | % Solubility | Western blot reactivity** | | | |
|---|---|---|---|---|---|---|---|---|
| | | | | | His6Tag | Human | Rat | Rabbit |
| 1 | PG32 (aa21-391) | ++ | 43.8 | Insoluble | + | − | + | + |
| 2 | PG33 (aa22-380) | + | 43 | Insoluble | + | − | + | + |
| 3 | PG32 (aa21-223) | ++ | 22.6 | Insoluble | + | − | − | − |
| 4 | PG33 (aa22-212) | +++ | 21.2 | Insoluble | + | − | − | − |
| 5 | PG32 (aa86-223) | ++++ | 15.4 | 10% | + | − | − | +/− |
| 6 | PG33 (aa84-212) | + | 14.3 | Insoluble | + | − | − | + |
| 7 | PG32 (aa21-152) | + | 14.6 | Insoluble | + | − | − | + |
| 8 | PG33 (aa22-150) | +++++ | 14.3 | Insoluble | + | − | − | − |
| 9 | PG32 (aa153-306) | ++ | 17.2 | Insoluble | + | − | − | + |
| 10 | PG33 (aa151-285) | + | 15 | Insoluble | + | − | − | + |
| 11 | PG32 (aa191-322) | +++++ | 14.6 | 10% | + | − | − | +/− |
| 12 | PG33 (aa193-310) | +++ | 10.9 | <5% | + | − | +/− | + |
| 13 | PG32 (aa86-306) | +++++ | 24.6 | Insoluble | + | − | +/− | + |
| 14 | PG33 (aa84-285) | +++ | 22.4 | Insoluble | + | − | − | + |
| 15 | PG32 (aa86-322) | ++++ | 26.3 | Insoluble | + | − | +/− | + |
| 16 | PG33 (aa84-310) | ++++ | 25.2 | Insoluble | + | − | +/− | + |
| 17 | PG32 (aa153-322) | + | 18.4 | Insoluble | + | − | − | − |
| 18 | PG33 (aa151-310) | ++++ | 17.7 | Insoluble | + | − | +/− | + |
| 19 | PG32 (aa191-306) | ++++ | 13 | <5% | + | − | − | + |
| 20 | PG33 (aa193-285) | +++++ | 8.1 | Insoluble | + | − | +/− | + |
| 21 | PG32 (aa224-391) | ++++++ | 18.5 | 10–15% | + | − | + | + |
| 22 | PG33 (aa213-380) | +++++ | 18.6 | 10–15% | + | − | + | + |
| 23 | PG33 (aa286-380) | +++ | 10.5 | <5% | + | − | − | + |
| 24 | PG32 (aa224-306) | +++ | 9.3 | 20% | + | − | − | +/− |
| 25 | PG33 (aa213-285) | +++ | 8.1 | <5% | + | − | − | + |
| 26 | PG32 (aa281-384) | +++++ | 11.4 | 50% | + | − | − | + |
| 27 | PG33 (aa306-372) | ++ | 7.3 | 10% | + | − | − | − |

*Expression levels; + = low level through to ++++++ = Extremely high levels of expression
**Western blot reactivity; +/− = low level reactivity + = Clearly positive reactivity

EXAMPLE 3

Murine Lesion Model

Groups of 10 female BALB/c mice (6–8 weeks old) were immunized (20 µg/dose) subcutaneously with each recombinant protein, PG32 (Construct 1 in 0.5M urea), PG33 (Construct 2 in 2M urea), PG32 fragment (Construct 21) and PG33 fragment (Construct 22). Control mice were given formalin-killed *P. gingivalis* cells (approximately 2×10$^9$, or *E. coli* lysate (20 µg/dose); all emulsified in Incomplete Freunds Adjuvant (SIGMA). The immunizations were given subcutaneously at the base of the tail and occurred four weeks and one week prior to challenge with *P. gingivalis*. Two days prior to challenge mice were bled from the retrobulbar plexus. BALB/c mice were challenged with 7.5×10$^9$ viable cells of *P. gingivalis* 33277 subcutaneously into the ventral region of the abdomen. Following challenge, mice were examined daily for the number and size of lesions over a period of seven days. Lesions developed on the abdomen of the mice around the injection site and the lesions were measured daily.

Figure 1B:
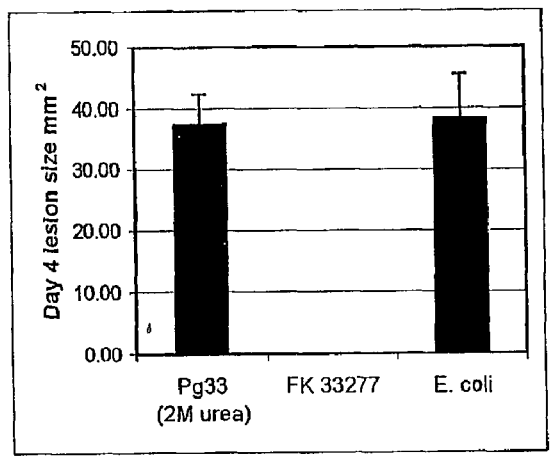
Figure 1C:
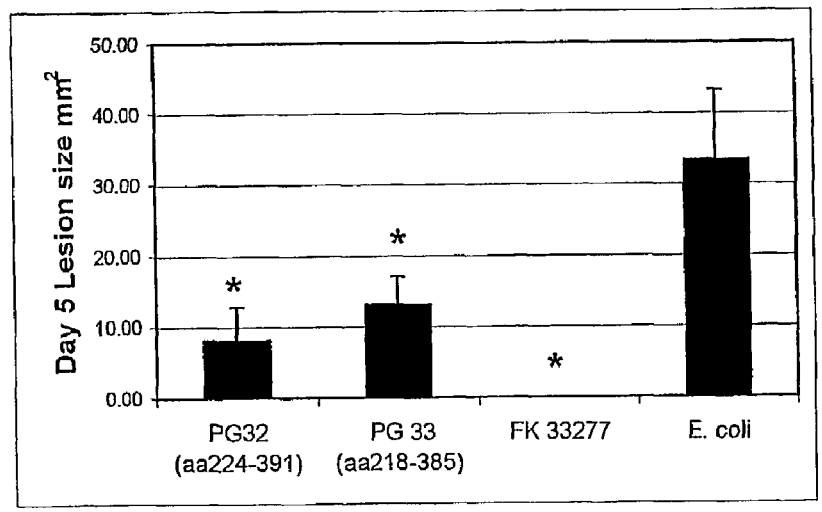

FIG. 1 shows the results from 3 separate experiments in which full length r-PG32 (Construct 1; aa21–391 in 0.5 M urea) FIG. 1a; and full length r-PG33 (Construct 2;

aa22–380 in 2M urea) FIG. 1b; were used to immunise mice and compared to fragments of r-PG32 (Construct 21; aa224–391 in PBS) and r-PG33 (Construct 22; aa213–380 in PBS), FIG. 1c. Control mice were given formalin killed P. gingivalis strain 33277 whole cells (FK 33277) or whole E. coli lysate (E. coli). Significant reductions in lesion size were obtained only with vaccination using formalin-killed whole P. gingivalis cells (strain 33277) and the fragments from r-PG32 (Construct 21; aa 224–391 in PBS, $p<0.01$) and r-PG33 (Construct 22; aa 213–380 in PBS, $p<0.05$).

EXAMPLE 4

Expression of PG32 (aa224–391) in Yeast

Cloning of PG32 fragment (aa224–391). PG32 (Construct 21) was PCR amplified and extracted as outlined in Example 1. The purified DNA was ligated into QIAEXII purified yeast GST expression vector pYEX4T-1 (Amrad) that had been previously digested with EcoRI and NotI. The ligation product was transformed into calcium competent E. coli BL21 DE3 (STRATAGENE) and selected on LB plates containing 50 μg ampicillin. A single colony of E. coli cells containing the recombinant plasmid was inoculated into a 100 ml culture containing Terrific broth containing ampicillin overnight and the plasmid purified with a QIAGEN Plasmid Maxi Kit before being transformed into yeast.

Yeast transformation. A sample of S. cerevisiae DY150 glycerol stock was streaked out onto a YPD plate and placed at 30° C. for 3–4 days. A single colony was inoculated into 20 ml YPD medium and shaken at 30° C. for 24 hrs. A 500 μl volume of the overnight culture was centrifuged at 3000 rpm for 5 mm and the DY 150 pellet was washed in 1 ml of dH2O. The pellet was resuspended in 10 mg/ml calf thymus DNA (SIGMA), to which was added 1 ug of plasmid DNA along with 500 ul of plate solution, and the mixture was incubated at 25° C. for 24 hrs. Cells were spun at 3000 rpm for 5 min and the plate solution was removed. Yeast was washed in 1 ml of dH2O, plated out on a YNBS plate and incubated at 30° C. for 4–5 days.

Small-scale expression in yeast. A single colony transformant was used to inoculate 5 ml of YNBS broth and shaken at 30° C. for 48 hrs. A 0.5 ml inoculum was added to 5 ml of fresh YNBS broth and induced with 0.5 mM CuSO4. After a 3 hr induction period at 30° C. the culture was harvested by centrifugation and resuspended in 500 ul breaking buffer (containing 1 mM PMSF and 10 mM E-64, SIGMA). A 2.0 ml screw cap vial (BIOSPEC) was filled three quarters full with 0.5 mm glass beads (BIOSPEC) and the remaining vial volume was filled with cells. The mixture was homogenised in a mini-beadbeater cell disrupter (BIOSPEC) for 8×30 sec (5,000 rpm) with a 30 sec incubation on ice between runs. The beads were left to settle and the broken yeast cells were recovered. Following centrifugation for 5 minutes (3,000 g) the supernatant was collected and represented the soluble fraction. The pellet was resuspended in breaking buffer to produce the insoluble fraction. Fractions were analysed using SDS-PAGE and Western blot analysis.

Figure 2A:
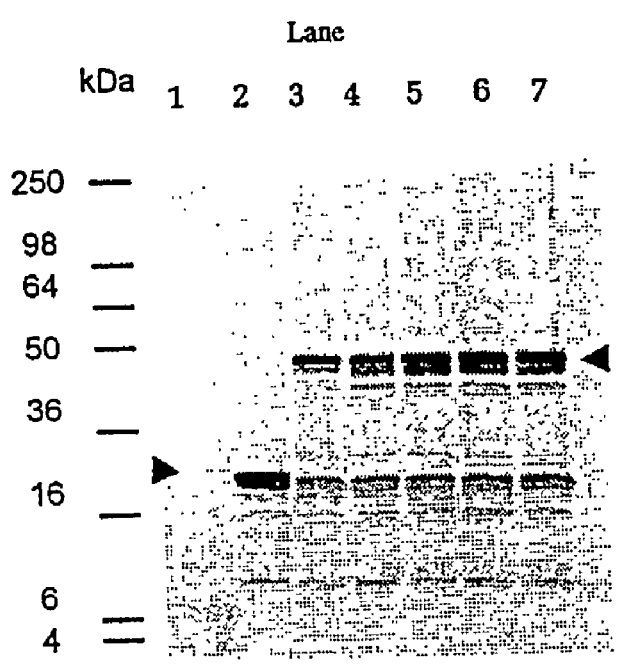
FIGS. 2A and 2B show Western blots of a 12% SDS-PAGE gel (NOVEX) reacted with a mouse monoclonal anti-GST (B14; SANTA CRUZ BIOTECHNOLOGY) (FIG. 2*a*) and a blot reacted with sera from mice immunised with PG32 (aa224–391) in FIA (FIG. 2*b*). Bound antibody was traced using a Sheep anti-mouse Ig-HRP sera at 1:2000 (SILENUS) and detected with TMB membrane peroxidase substrate (KPL).
Figure 2B:
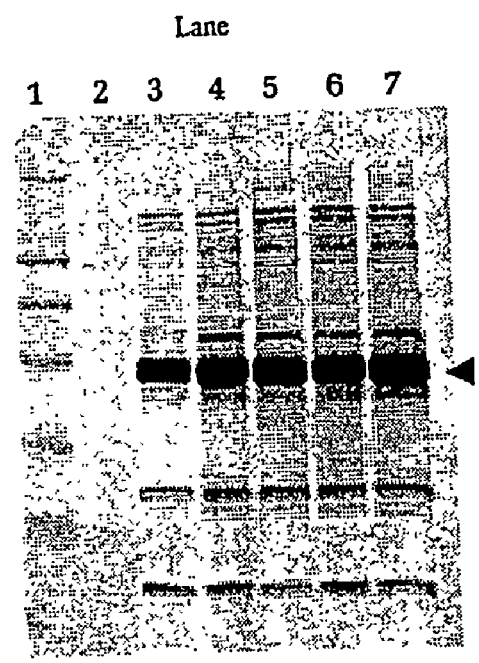

The results of the yeast expression of the PG32 fragment (aa224–391) are shown in FIGS. 2a and 2b. Lane 1 in both figures contains pre-stained molecular weight markers (NOVEX, SEEBLUE) while Lane 2 contains supernatant from disrupted recombinant yeast expressing only GST. Lanes 3–7 represent expanded individual clones of disrupted yeast cells containing GST fused with the PG32 gene (aa224–391) without (lane 3) and with the PG32 gene optimised for yeast codon usage (lanes 4–7, see Example 5). Note that reactivity is seen only at the position of GST alone (Lane 2, FIG. 2a see arrow at approximately 27.5 kDa) when the membrane was probed with anti-GST, compared to the dominant higher molecular weight band seen when the GST was fused with PG32 (aa224–391), lanes 3–7 (note arrow at approximately 48 kDa in FIG. 2a). When the Western blot was reacted with the anti-PG32 antisera (FIG. 2b) no reactivity was seen in yeast expressing GST alone (lane2) but strong reactivity was seen at approximately 46–48 kDa (see arrow) with some reactivity with other bands. The predicted molecular weight for the fusion protein was approximately 46 kDa and this corresponds to the strongly staining band in lanes 3–7 (FIG. 2b indicated by the arrow).

EXAMPLE 5

Construction and Cloning of Synthetic PG32 (aa224–391) for Optimum Protein Expression in Yeast.

A synthetic PG32 truncated gene (corresponding to PG32 aa224–391) was constructed using the predicted S. cerevisiae codon usage to improve the expression of P. gingivalis proteins in S. cerevisiae. Oligonucleotides covering the entire double stranded DNA sequence, as listed in Table 4 were designed with high expression bias codons for expression in yeast (Sharp, P. M., and Cowe, E. (1991) Yeast. 7, 657–678). The oligonucleotide primers A and B were converted to a dsDNA fragment by PCR with TAQPLUS PRECISION (STRATAGENE) DNA polymerase using the following conditions: 20 cycles of denaturation (96° C., 1 min), annealing (53° C., 1 min), and extension (72° C., 2 min), with the duration of the extension step increased by 5 sec at each cycle (Di Donato, A., de Nigris, M., Russo, N., Di Biase, S., and D'Alessio, G. (1993) Analytical Biochemistry. 212, 291–293). A {fraction (1/20)} aliquot of the core mixture was used in a second PCR run with oligonucleotide primers C and D functioning to elongate the core template. The procedure was repeated, with each primer pair until the 500 bp product was generated. This PCR product was proteinase K treated (BOEHRINGER MANNHEIM), purified using the QUICK PCR purification kit (QIAGEN and digested at the primer introduced restriction enzyme sites EcoRI and NotI. The DNA fragment was purified by electrophoresis through a 1% low melting agarose gel (BIO-RAD) and extracted using the QIAEXII gel extraction kit (QIAGEN). The purified DNA was ligated into QIAEXII purified yeast GST expression vector pYEX4T-1 (AMRAD) that had been previously digested with EcoRI and NotI. The ligation products were transformed into calcium competent E. coli BL21 DE3 (STRATAGENE) and selected on LB plates containing 50 μg ampicillin. The integrity of the codon replaced insert was confirmed by DNA sequence analysis. Transformation of yeast and the expression of PG32 was performed as outlined above. FIG. 2 shows the expression and immunoreactivity of yeast expressed synthetic PG32 (aa224–391) fused with GST. In FIGS. 2a and 2b, Lane 3 contains the unmodified P. gingivalis codons expressed in yeast and lanes 4, 5, 6, 7 contain clones which have had their codons optimised for expression in yeast as outlined above. There appeared to be some enhanced expression and immunoreactivity when the codon optimisation was undertaken as evidenced by the increased reactivity in the bands at approximately 48 kD (see arrows) especially when the antisera to PG32 was used (FIG. 2b).

TABLE 4

Multiple overlapping oligonucleotide primers used for the generation of PG32C high expression bias codon replaced DNA.
Oligonucleotides for Synthetic PG32-C

| Oligonucleotide DNA Sequence (5'→3') | | SEQ ID NO. |
|---|---|---|
| A (62-mer) | AC Overlap | |
| | GGCTGTTTTGTTCAGATTCGATTCTCACGTTGTT | 31 |
| | GATAAGGATCAATTGATTAACTTGTACG | 32 |
| | AB Overlap | |
| B (57-mer) | BD Overlap | |
| | GGTTCGTTAGTTTCCTTAACGAATTGAGCAACA | 33 |
| | TCGTACAAGTTAATCAATTGATCC | 34 |
| | BA Overlap | |
| C (62-mer) | CE Overlap | |
| | CCAGAAGTTACTCCAGTTACTAAGACTGAAAA | 35 |
| | CATTTTGACTGAAAAGGCTGTTTTGTTCAG | 36 |
| | CA Overlap | |
| D (61-mer) | DF Overlap | |
| | GTATTGAGTGTTACCAGTTGGATCAGCGTAACC | 37 |
| | AACAACAGTAATTGGTTCGTTAGTTTCC | 38 |
| | DB Overlap | |
| E (60-mer) | EG Overlap | |
| | GAAGTTGAAGAATTGTCTAAGAGACCAGTTTCT | 39 |
| | TGTCCAGAATGTCCAGAAGTTACTCCA | 40 |
| | EC Overlap | |
| F (62-mer) | FH Overlap | |
| | AACATCAACAACAGCCTTAGCTCTTCTTTCAGA | 41 |
| | CAACTTTTCGTTGTATTGAGTGTTACCAG | 42 |
| | FD Overlap | |
| G (64-mer) | GI Overlap | |
| | CGCTTTGATTAACGATTTGAACGGTCAAATTAA | 43 |
| | CAGATTGAGATCTGAAGTTGAAGAATTGTCT | 44 |
| | GE Overlap | |
| H (64-mer) | HJ Overlap | |
| | CCATTCAACAGAAATCAATTCAGATGGAACAC | 45 |
| | CGTACTTACCAGTCAAAACATCAACAACAGCC | 46 |
| | HF Overlap | |
| I (54-mer) | IK Overlap | |
| | GTGCTGTTGGTTTCAACGCTATTGAACCAATGG | 47 |
| | ATTACGCTTTGATTAACGATT | 48 |
| | IG Overlap | |
| J (55-mer) | JL Overlap | |
| | CAAGCCTTCTTAGAGAATGGTTGAGTAGAATCA | 49 |
| | CCCTTCCATTCAACAGAAATCA | 50 |
| | JH Overlap | |
| K (54-mer) | EcoRI | |
| | GATCGAATTCGCTACTGCTGGTTTGAACTTCAG | 51 |
| | ATTGGGTGCTGTTGGTTTCAA | 52 |
| | KI Overlap | |
| L (55-mer) | Not I | |
| | CTATGCGGCCGCTTAGATCTAACAATAACAAC | 53 |
| | TCTGTTCCAAGCCTTCTTAGAGA | 54 |
| | LJ Overlap | |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A purified polypeptide of the formula X-Y-Z, wherein Y is a soluble *P. gingivalis* polypeptide fragment consisting of amino acid residues 224 to 391 of SEQ ID NO:3, X and Z are optional and consist of amino acids or peptides;
   wherein the purified polypeptide is soluble in a TE buffer having a pH of 8.0.

2. The purified polypeptide of claim 1, wherein Y is a biologically active *P. gingivalis* polypeptide fragment consisting of amino acid residues 224 to 391 of SEQ ID NO:3.

3. The purified polypeptide of claim 1, wherein X and/or Z are absent.

4. A purified *P. gingivalis* polypeptide, the polypeptide consisting essentially of amino acid residues 224 to 391 of SEQ ID NO:3;
   wherein the purified polypeptide is soluble in a TE buffer having a pH of 8.0.

5. A chimeric or fusion construct comprising the purified polypeptide of claim 1.

6. A composition for use in raising an immune response directed against *P. gingivalis* in a subject, the composition comprising the purified polypeptide as claimed in claim 1, and a pharmaceutically acceptable carrier.

7. The composition as claimed in claim 6 wherein the pharmaceutically acceptable carrier is an adjuvant.

8. A method of reducing the severity of *P. gingivalis* infection in a subject comprising administering to the subject the composition of claim 6.

9. A diagnostic method for detecting the presence or absence of an antibody specific to *P. gingivalis* in a sample, the method comprising contacting the sample with the purified polypeptide as of claim 1 under conditions sufficient for the polypeptide to form an immune complex with said antibody in the sample, and detecting the presence or absence of the immune complex.

10. A kit comprising the purified polypeptide of claim 1.

* * * * *

SEQUENCE LISTING

<160> NUMBER OF SEQ ID NOS: 54

<210> SEQ ID NO 1
<211> LENGTH: 1176
<212> TYPE: DNA
<213> ORGANISM: Porphyromonas gingivalis

<400> SEQUENCE: 1

| | | | |
|---|---|---|---|
| atgaaggtaa agtacttaat gctcacattg gttggagcaa ttgcactgaa cgcaagtgca | 60 |
| caggagaata ctgtaccggc aacgggtcag ttacccgcta agaatgttgc ttttgctcgc | 120 |
| aataaagcag gcagcaattg gtttgtaaca ctgcaaggcg gtgttgcagc gcagttcctc | 180 |
| aatgacaaca caacaaaga cctcatggac cgcttaggag ccataggttc tctttctgtc | 240 |
| ggaaagtatc acagcccttt ctttgcaact cgtttgcaaa ttaacggagg tcaagcccac | 300 |
| actttcctcg gaaaaaatgg cgaacaagaa atcaacacca attttggtgc agctcacttc | 360 |
| gactttatgt ttgatgtggt taactacttt gcaccatatc gcgaaaatcg tttcttccat | 420 |
| ttaattccat gggtaggtgt tggctaccaa cacaaattca tcggtagcga atggagcaaa | 480 |
| gacaatgtgg aatcactgac ggcgaatgta ggagttatga tggctttcag attaggaaag | 540 |
| cgagtagact ttgtgatcga agcacaagca gctcactcca atctcaatct aagtcgcgca | 600 |
| tacaatgcca agaaaactcc cgtattcgaa gatcccgcag gacgttatta caatggattc | 660 |
| cagggggatgg ctacagcagg tcttaatttc cgcctgggag ccgtaggctt caatgccatt | 720 |
| gaaccaatgg actacgcact tatcaatgat ctgaatggtc agattaaccg tttgcgcagc | 780 |
| gaggtcgaag aactctcaaa acgtcctgta tcatgcccg aatgtcctga agtaactcct | 840 |
| gttactaaga cagaaaatat actgacggaa aaagctgtac tgttccgttt cgacagccac | 900 |
| gttgtggaca agatcaatt gatcaacctg tatgacgtag ctcagtttgt aaaagaaact | 960 |
| aacgagccga ttaccgttgt tggttatgct gatcctacgg gtaatactca atacaacgag | 1020 |
| aaattgtctg agcgtcgggc taaagccgtt gttgatgttc tgacaggtaa atatggtgtg | 1080 |
| ccttccgaat taatctctgt agaatggaag ggcgactcta cgcaaccgtt cagcaagaaa | 1140 |
| gcttggaatc gtgttgtaat cgttcgctcc aagtaa | 1176 |

<210> SEQ ID NO 2
<211> LENGTH: 1140
<212> TYPE: DNA
<213> ORGANISM: Porphyromonas gingivalis

<400> SEQUENCE: 2

| | | | |
|---|---|---|---|
| atgaaagcta atctttatt attagcactt gcgggtctcg catgcacatt cagtgcaaca | 60 |
| gcccaagaag ctactacaca gaacaaagca gggatgcaca ccgcattcca acgtgataag | 120 |
| gcctccgatc attggttcat tgacattgca ggtggagcag gtatggctct ctcgggatgg | 180 |
| aataatgatg tagactttgt agatcgtcta agtatcgttc ctactttcgg tatcggtaaa | 240 |
| tggcatgagc cttatttcgg tactcgtctc caattcacag gattcgacat ctatggattc | 300 |
| ccgcaaggga gcaaggagcg taaccacaat tactttggaa acgcccacct tgacttcatg | 360 |
| ttcgatctga cgaactattt cggtgtatac cgtcccaatc gtgtcttcca tatcatccca | 420 |
| tgggcaggta taggatttgg ttataaattc catagcgaaa acgccaatgg tgaaaaagta | 480 |
| ggaagtaaag atgatatgac cggaacagtt aatgtcggtt tgatgctgaa attccgccta | 540 |
| tcaagagtcg tagacttcaa tattgaagga caagcttttg ccggaaagat gaactttatc | 600 |

-continued

```
gggacaaaga gaggaaaagc agacttccct gtaatggcta cagcaggtct aacgttcaac    660
cttggcaaga cagagtggac agaaattgtt cctatggact atgctttggt caatgacctg    720
aacaaccaaa tcaactcact tcgcggtcaa gtggaagagt tgagccgtcg tcctgtttca    780
tgccctgaat gccctgagcc tacacagcct acagttactc gtgtagtcgt tgacaatgtg    840
gtttacttcc gtatcaatag tgcaaagatt gatcgtaatc aagaaatcaa tgtttacaat    900
acagctgaat atgcgaagac caacaacgca ccgatcaagg tagtaggtta cgctgacgaa    960
aaaaccggta ctgcggccta acatgaagc tttcagagc gtcgtgcaaa agcggtagcc    1020
aagatgcttg aaaagtatgg tgtttctgcg gatcgcatta caattgaatg gaagggctca    1080
tcagagcaaa tctatgaaga gaacgcttgg aatcgtattg tagtaatgac tgcagcggaa    1140
```

<210> SEQ ID NO 3
<211> LENGTH: 391
<212> TYPE: PRT
<213> ORGANISM: Porphyromonas gingivalis

<400> SEQUENCE: 3

```
Met Lys Val Lys Tyr Leu Met Leu Thr Leu Val Gly Ala Ile Ala Leu
 1               5                   10                  15

Asn Ala Ser Ala Gln Glu Asn Thr Val Pro Ala Thr Gly Gln Leu Pro
            20                  25                  30

Ala Lys Asn Val Ala Phe Ala Arg Asn Lys Ala Gly Arg Asn Trp Phe
        35                  40                  45

Val Thr Leu Gln Gly Gly Val Ala Ala Gln Phe Leu Asn Asp Asn Asn
    50                  55                  60

Asn Lys Asp Leu Met Asp Arg Leu Gly Ala Ile Gly Ser Leu Ser Val
65                  70                  75                  80

Gly Lys Tyr His Ser Pro Phe Phe Ala Thr Arg Leu Gln Ile Asn Gly
                85                  90                  95

Gly Gln Ala His Thr Phe Leu Gly Lys Asn Gly Glu Gln Glu Ile Asn
            100                 105                 110

Thr Asn Phe Gly Ala Ala His Phe Asp Phe Met Phe Asp Val Val Asn
        115                 120                 125

Tyr Phe Ala Pro Tyr Arg Glu Asn Arg Phe Phe His Leu Ile Pro Trp
    130                 135                 140

Val Gly Val Gly Tyr Gln His Lys Phe Ile Gly Ser Glu Trp Ser Lys
145                 150                 155                 160

Asp Asn Val Glu Ser Leu Thr Ala Asn Val Gly Val Met Met Ala Phe
                165                 170                 175

Arg Leu Gly Lys Arg Val Asp Phe Val Ile Glu Ala Gln Ala Ala His
            180                 185                 190

Ser Asn Leu Asn Leu Ser Arg Ala Tyr Asn Ala Lys Lys Thr Pro Val
        195                 200                 205

Phe Glu Asp Pro Ala Gly Arg Tyr Tyr Asn Gly Phe Gln Gly Met Ala
    210                 215                 220

Thr Ala Gly Leu Asn Phe Arg Leu Gly Ala Val Gly Phe Asn Ala Ile
225                 230                 235                 240

Glu Pro Met Asp Tyr Ala Leu Ile Asn Asp Leu Asn Gly Gln Ile Asn
                245                 250                 255

Arg Leu Arg Ser Glu Val Glu Glu Leu Ser Lys Arg Pro Val Ser Cys
            260                 265                 270

Pro Glu Cys Pro Glu Val Thr Pro Val Thr Lys Thr Glu Asn Ile Leu
```

```
            275                 280                 285
Thr Glu Lys Ala Val Leu Phe Arg Phe Asp Ser His Val Val Asp Lys
    290                 295                 300

Asp Gln Leu Ile Asn Leu Tyr Asp Val Ala Gln Phe Val Lys Glu Thr
305                 310                 315                 320

Asn Glu Pro Val Thr Val Gly Tyr Ala Asp Pro Thr Gly Asn Thr
                325                 330                 335

Gln Tyr Asn Glu Lys Leu Ser Glu Arg Arg Ala Lys Ala Val Val Asp
            340                 345                 350

Val Leu Thr Gly Lys Tyr Gly Val Pro Ser Glu Leu Ile Ser Val Glu
        355                 360                 365

Trp Lys Gly Asp Ser Thr Gln Pro Phe Ser Lys Ala Trp Asn Arg
370                 375                 380

Val Val Ile Val Arg Ser Lys
385                 390

<210> SEQ ID NO 4
<211> LENGTH: 380
<212> TYPE: PRT
<213> ORGANISM: Porphyromonas gingivalis

<400> SEQUENCE: 4

Met Lys Ala Lys Ser Leu Leu Ala Leu Ala Gly Leu Ala Cys Thr
1               5                   10                  15

Phe Ser Ala Thr Ala Gln Glu Ala Thr Thr Gln Asn Lys Ala Gly Met
                20                  25                  30

His Thr Ala Phe Gln Arg Asp Lys Ala Ser Asp His Trp Phe Ile Asp
            35                  40                  45

Ile Ala Gly Gly Ala Gly Met Ala Leu Ser Gly Trp Asn Asn Asp Val
    50                  55                  60

Asp Phe Val Asp Arg Leu Ser Ile Val Pro Thr Phe Gly Ile Gly Lys
65                  70                  75                  80

Trp His Glu Pro Tyr Phe Gly Thr Arg Leu Gln Phe Thr Gly Phe Asp
                85                  90                  95

Ile Tyr Gly Phe Pro Gln Gly Ser Lys Glu Arg Asn His Asn Tyr Phe
            100                 105                 110

Gly Asn Ala His Leu Asp Phe Met Phe Asp Leu Thr Asn Tyr Phe Gly
        115                 120                 125

Val Tyr Arg Pro Asn Arg Val Phe His Ile Ile Pro Trp Ala Gly Ile
    130                 135                 140

Gly Phe Gly Tyr Lys Phe His Ser Glu Asn Ala Asn Gly Glu Lys Val
145                 150                 155                 160

Gly Ser Lys Asp Asp Met Thr Gly Thr Val Asn Val Gly Leu Met Leu
                165                 170                 175

Lys Phe Arg Leu Ser Arg Val Val Asp Phe Asn Ile Glu Gly Gln Ala
            180                 185                 190

Phe Ala Gly Lys Met Asn Phe Ile Gly Thr Lys Arg Gly Lys Ala Asp
        195                 200                 205

Phe Pro Val Met Ala Thr Ala Gly Leu Thr Phe Asn Leu Gly Lys Thr
    210                 215                 220

Glu Trp Thr Glu Ile Val Pro Met Asp Tyr Ala Leu Val Asn Asp Leu
225                 230                 235                 240

Asn Asn Gln Ile Asn Ser Leu Arg Gly Gln Val Glu Glu Leu Ser Arg
                245                 250                 255
```

```
Arg Pro Val Ser Cys Pro Glu Cys Pro Glu Pro Thr Gln Pro Thr Val
            260                 265                 270

Thr Arg Val Val Val Asp Asn Val Val Tyr Phe Arg Ile Asn Ser Ala
            275                 280                 285

Lys Ile Asp Arg Asn Gln Glu Ile Asn Val Tyr Asn Thr Ala Glu Tyr
            290                 295                 300

Ala Lys Thr Asn Asn Ala Pro Ile Lys Val Val Gly Tyr Ala Asp Glu
305                 310                 315                 320

Lys Thr Gly Thr Ala Ala Tyr Asn Met Lys Leu Ser Glu Arg Arg Ala
                325                 330                 335

Lys Ala Val Ala Lys Met Leu Glu Lys Tyr Gly Val Ser Ala Asp Arg
            340                 345                 350

Ile Thr Ile Glu Trp Lys Gly Ser Ser Glu Gln Ile Tyr Glu Glu Asn
            355                 360                 365

Ala Trp Asn Arg Ile Val Val Met Thr Ala Ala Glu
    370                 375                 380

<210> SEQ ID NO 5
<211> LENGTH: 34
<212> TYPE: DNA
<213> ORGANISM: Porphyromonas gingivalis

<400> SEQUENCE: 5
cgcagaattc caggagaata ctgtaccggc aacg                                 34

<210> SEQ ID NO 6
<211> LENGTH: 35
<212> TYPE: DNA
<213> ORGANISM: Porphyromonas gingivalis

<400> SEQUENCE: 6
ctatgcggcc gccttggagc gaacgattac aacac                                35

<210> SEQ ID NO 7
<211> LENGTH: 34
<212> TYPE: DNA
<213> ORGANISM: Porphyromonas gingivalis

<400> SEQUENCE: 7
tgcagaattc caagaagcta ctacacagaa caaa                                 34

<210> SEQ ID NO 8
<211> LENGTH: 36
<212> TYPE: DNA
<213> ORGANISM: Porphyromonas gingivalis

<400> SEQUENCE: 8
ctatgcggcc gcttccgctg cagtcattac ttacaa                               36

<210> SEQ ID NO 9
<211> LENGTH: 30
<212> TYPE: DNA
<213> ORGANISM: Porphyromonas gingivalis

<400> SEQUENCE: 9
ttttgcggcc gccatcccct ggaatccatt                                      30

<210> SEQ ID NO 10
<211> LENGTH: 34
<212> TYPE: DNA
<213> ORGANISM: Porphyromonas gingivalis
```

-continued

<400> SEQUENCE: 10
tgcagaattc caagaagcta ctacacagaa caaa                                34

<210> SEQ ID NO 11
<211> LENGTH: 30
<212> TYPE: DNA
<213> ORGANISM: Porphyromonas gingivalis

<400> SEQUENCE: 11
ttttgcggcc gccattacag ggaagtctgc                                     30

<210> SEQ ID NO 12
<211> LENGTH: 28
<212> TYPE: DNA
<213> ORGANISM: Porphyromonas gingivalis

<400> SEQUENCE: 12
ttttgaattc cctttctttg caactcgt                                       28

<210> SEQ ID NO 13
<211> LENGTH: 28
<212> TYPE: DNA
<213> ORGANISM: Porphyromonas gingivalis

<400> SEQUENCE: 13
ttttgaattc ccttatttcg gtactcgt                                       28

<210> SEQ ID NO 14
<211> LENGTH: 30
<212> TYPE: DNA
<213> ORGANISM: Porphyromonas gingivalis

<400> SEQUENCE: 14
aaaagcggcc gctttgtgtt ggtagccaac                                     30

<210> SEQ ID NO 15
<211> LENGTH: 30
<212> TYPE: DNA
<213> ORGANISM: Porphyromonas gingivalis

<400> SEQUENCE: 15
aaaagcggcc gcgaatttat aaccaaatcc                                     30

<210> SEQ ID NO 16
<211> LENGTH: 28
<212> TYPE: DNA
<213> ORGANISM: Porphyromonas gingivalis

<400> SEQUENCE: 16
ttttgaattc ttcatcggta gcgaatgg                                       28

<210> SEQ ID NO 17
<211> LENGTH: 29
<212> TYPE: DNA
<213> ORGANISM: Porphyromonas gingivalis

<400> SEQUENCE: 17
ttttgcggcc gccaattgat ctttgtcca                                      29

<210> SEQ ID NO 18
<211> LENGTH: 27
<212> TYPE: DNA

<213> ORGANISM: Porphyromonas gingivalis

<400> SEQUENCE: 18
ttttgaattc catagcgaaa acgccaa    27

<210> SEQ ID NO 19
<211> LENGTH: 30
<212> TYPE: DNA
<213> ORGANISM: Porphyromonas gingivalis

<400> SEQUENCE: 19
ttttgcggcc gcgatacgga agtaaaccac    30

<210> SEQ ID NO 20
<211> LENGTH: 28
<212> TYPE: DNA
<213> ORGANISM: Porphyromonas gingivalis

<400> SEQUENCE: 20
ttttgaattc gctcactcca atctcaat    28

<210> SEQ ID NO 21
<211> LENGTH: 30
<212> TYPE: DNA
<213> ORGANISM: Porphyromonas gingivalis

<400> SEQUENCE: 21
aaaagcggcc gcctcgttag tttcttttac    30

<210> SEQ ID NO 22
<211> LENGTH: 28
<212> TYPE: DNA
<213> ORGANISM: Porphyromonas gingivalis

<400> SEQUENCE: 22
ttttgaattc tttgccggaa agatgaac    28

<210> SEQ ID NO 23
<211> LENGTH: 30
<212> TYPE: DNA
<213> ORGANISM: Porphyromonas gingivalis

<400> SEQUENCE: 23
aaaagcggcc gctgcgttgt tggtcttcgc    30

<210> SEQ ID NO 24
<211> LENGTH: 32
<212> TYPE: DNA
<213> ORGANISM: Porphyromonas gingivalis

<400> SEQUENCE: 24
gatcgaattc gctacagcag gtcttaattt cc    32

<210> SEQ ID NO 25
<211> LENGTH: 33
<212> TYPE: DNA
<213> ORGANISM: Porphyromonas gingivalis

<400> SEQUENCE: 25
gatcgaattc gctacagcag gtctaacgtt caa    33

<210> SEQ ID NO 26
<211> LENGTH: 30

```
<212> TYPE: DNA
<213> ORGANISM: Porphyromonas gingivalis

<400> SEQUENCE: 26
gatccgaatt cgaatagtgc aaagattgat                                      30

<210> SEQ ID NO 27
<211> LENGTH: 32
<212> TYPE: DNA
<213> ORGANISM: Porphyromonas gingivalis

<400> SEQUENCE: 27
gatcgaattc actaagacag aaaatatact ga                                   32

<210> SEQ ID NO 28
<211> LENGTH: 30
<212> TYPE: DNA
<213> ORGANISM: Porphyromonas gingivalis

<400> SEQUENCE: 28
ttttgcggcc gcacgattcc aagctttctt                                      30

<210> SEQ ID NO 29
<211> LENGTH: 32
<212> TYPE: DNA
<213> ORGANISM: Porphyromonas gingivalis

<400> SEQUENCE: 29
gatcgaattc aagaccaaca acgcaccgat ca                                   32

<210> SEQ ID NO 30
<211> LENGTH: 30
<212> TYPE: DNA
<213> ORGANISM: Porphyromonas gingivalis

<400> SEQUENCE: 30
ttttgcggcc gcacgattcc aagcgttctc                                      30

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
ggctgttttg ttcagattcg attctcacgt tgtt                                 34

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
gataaggatc aattgattaa cttgtacg                                        28

<210> SEQ ID NO 33
<211> LENGTH: 33
<212> TYPE: DNA
<213> ORGANISM: Artificial Sequence
<220> FEATURE:
```

```
<223> OTHER INFORMATION: Description of Artificial Sequence:
      Oligonucleotide

<400> SEQUENCE: 33
ggttcgttag tttccttaac gaattgagca aca                              33

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34
tcgtacaagt taatcaattg atcc                                       24

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35
ccagaagtta ctccaggtac taagactgaa aa                              32

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36
cattttgact gaaaaggctg ttttgttcag                                 30

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
gtattgagtg ttaccagttg gatcagcgta acc                             33

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 38
aacaacagta attggttcgt tagtttcc                                   28

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence:
```

Oligonucleotide

<400> SEQUENCE: 39
gaagttgaag aattgtctaa gagaccagtt tct                          33

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
tgtccagaat gtccagaagt tactcca                                 27

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
aacatcaaca acagccttag ctcttctttc aga                          33

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42 caactttcg ttgtattgag tgttaccag                                29

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
cgctttgatt aacgatttga acggtcaaat taa                          33

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 44
cagattgaga tctgaagttg aagaattgtc t                            31

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

```
<400> SEQUENCE: 45
ccattcaaca gaaatcaatt cagatggaac ac                                    32

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 46
cgtacttacc agtcaaaaca tcaacaacag cc                                    32

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
gtgctgttgg tttcaacgct attgaaccaa tgg                                   33

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
attacgcttt gattaacgat t                                                21

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 49
caagccttct tagagaatgg ttgagtagaa tca                                   33

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 50
cccttccatt caacagaaat ca                                               22

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide
```

```
<400> SEQUENCE: 51
gatcgaattc gctactgctg gtttgaactt cag                                    33

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 52
attgggtgct gttggtttca a                                                 21

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 53
ctatgcggcc gcttagatct aacaataaca ac                                     32

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
tctgttccaa gccttcttag aga                                               23
```